United States Patent
Appelbaum

(10) Patent No.: US 10,517,693 B2
(45) Date of Patent: *Dec. 31, 2019

(54) DENTAL IMPLANT SCREWDRIVER HARNESS SYSTEM

(71) Applicant: Marc Appelbaum, Long Valley, NJ (US)

(72) Inventor: Marc Appelbaum, Long Valley, NJ (US)

( * ) Notice: Subject to any disclaimer, the term of this patent is extended or adjusted under 35 U.S.C. 154(b) by 289 days.

This patent is subject to a terminal disclaimer.

(21) Appl. No.: 15/808,210

(22) Filed: Nov. 9, 2017

(65) Prior Publication Data

US 2019/0133714 A1 May 9, 2019

(51) Int. Cl.
| | |
|---|---|
| A61B 90/53 | (2016.01) |
| A61C 19/00 | (2006.01) |
| A61C 8/00 | (2006.01) |
| A61C 1/14 | (2006.01) |
| A61C 1/08 | (2006.01) |
| A61C 5/48 | (2017.01) |

(52) U.S. Cl.
CPC ............ *A61B 90/53* (2016.02); *A61C 8/0089* (2013.01); *A61C 19/00* (2013.01); *A61C 1/084* (2013.01); *A61C 1/142* (2013.01); *A61C 5/48* (2017.02)

(58) Field of Classification Search
CPC ..... A61C 19/006; A61C 19/00; A61C 8/0089; A61C 1/082; A61C 1/084; A61C 1/124; A61C 5/40–48; A61C 1/142; A61B 90/53; A61B 17/663; A61B 17/666; B25B 23/02; B25B 23/08–12; B25B 15/00–06; B25B 23/00; B25B 23/0007; B25B 23/0035

USPC ............ 433/49, 163, 229; 206/63.5; 81/125, 81/450; 224/217, 218, 219, 220, 254; 248/51–52, 311.2, 311.3, 312, 312.1, 313

See application file for complete search history.

(56) References Cited

U.S. PATENT DOCUMENTS

| | | | | |
|---|---|---|---|---|
| 4,558,495 A | * | 12/1985 | Olsen | .................... B23B 45/006 24/16 PB |
| 4,643,674 A | * | 2/1987 | Zdarsky | ................... A61C 3/00 433/102 |

(Continued)

FOREIGN PATENT DOCUMENTS

| | | |
|---|---|---|
| DE | 202010002860 U1 | 12/2010 |
| FR | 842103 * | 6/1939 |

(Continued)

OTHER PUBLICATIONS

A. Ratnaditya et al., "A simplified method of preventing implant hex drive from aspiration or accidental swallowing during stage two implant recovery," Journal of International Society of Preventive and Community Dentistry 2014; 4, Suppl S1:23-5. Available from http://www.jispcd.org/text.asp?2014/4/4/23/144572.

*Primary Examiner* — Edward Moran
(74) *Attorney, Agent, or Firm* — Thomas J. Germinario

(57) ABSTRACT

A dental implant screwdriver harness system enables a dentist to restrain and stabilize an implant screwdriver, while simultaneously turning the driver head using only one hand. A tether attached to the dentist's hand/finger connects to a stepped socket assembly, comprising multiple driver sockets, which seat driver heads of several standard diameters. A flexible slotted driver shaft strap wraps over the driver shaft and holds the driver head down against a central socket base.

9 Claims, 8 Drawing Sheets

(56) References Cited

U.S. PATENT DOCUMENTS

| | | | |
|---|---|---|---|
| 5,016,795 A * | 5/1991 | Porteous | A61C 19/006 206/63.5 |
| 5,429,289 A | 7/1995 | Lamson et al. | |
| RE36,797 E | 8/2000 | Eggert et al. | |
| 6,216,319 B1 | 4/2001 | Elkins | |
| 2005/0087044 A1* | 4/2005 | Risolio | B25B 13/481 81/177.3 |
| 2010/0000381 A1* | 1/2010 | Takahashi | A61C 1/00 81/450 |
| 2011/0132944 A1 | 6/2011 | Gravitis | |

FOREIGN PATENT DOCUMENTS

| | | | | |
|---|---|---|---|---|
| FR | 2221114 A1 * | 10/1974 | | A61C 1/148 |
| FR | 2415454 A1 * | 8/1979 | | A61C 19/04 |

* cited by examiner

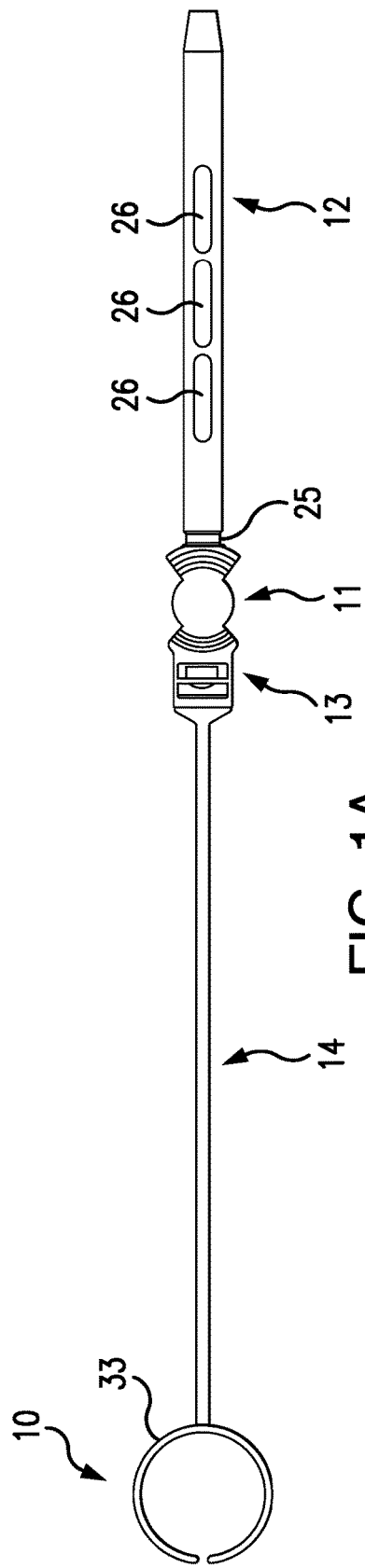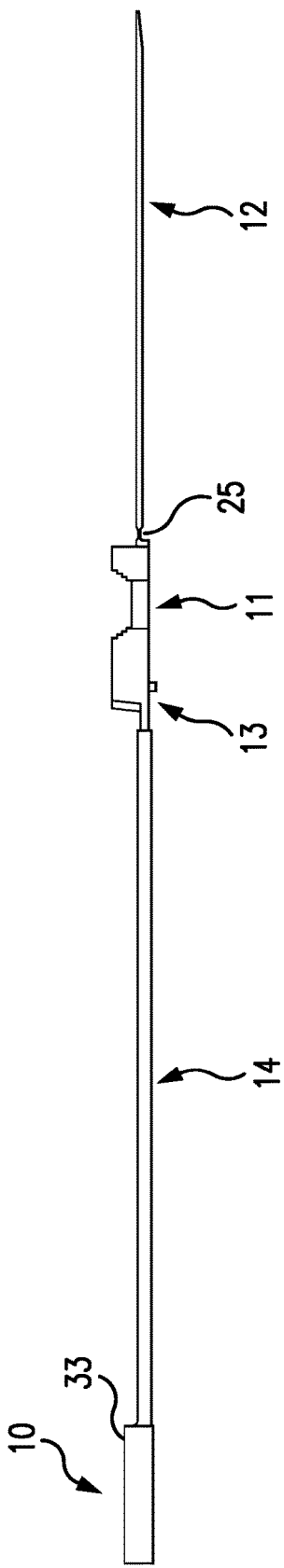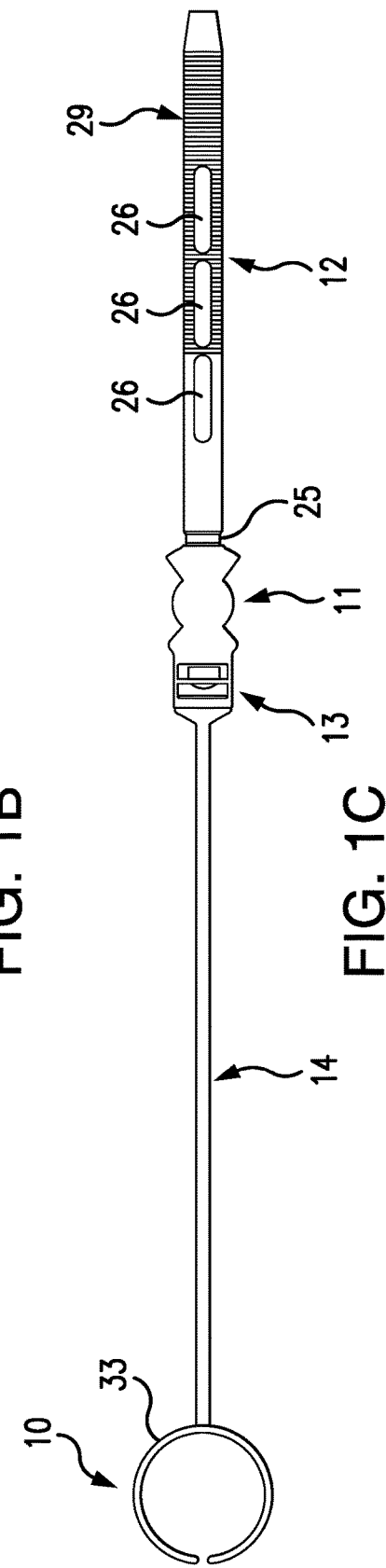

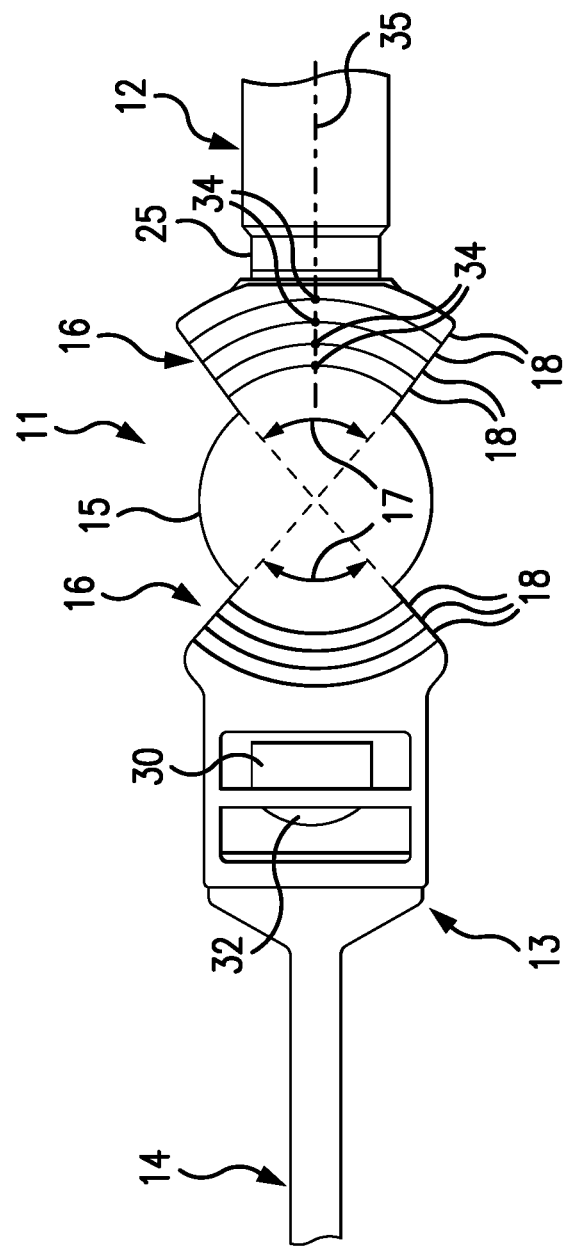

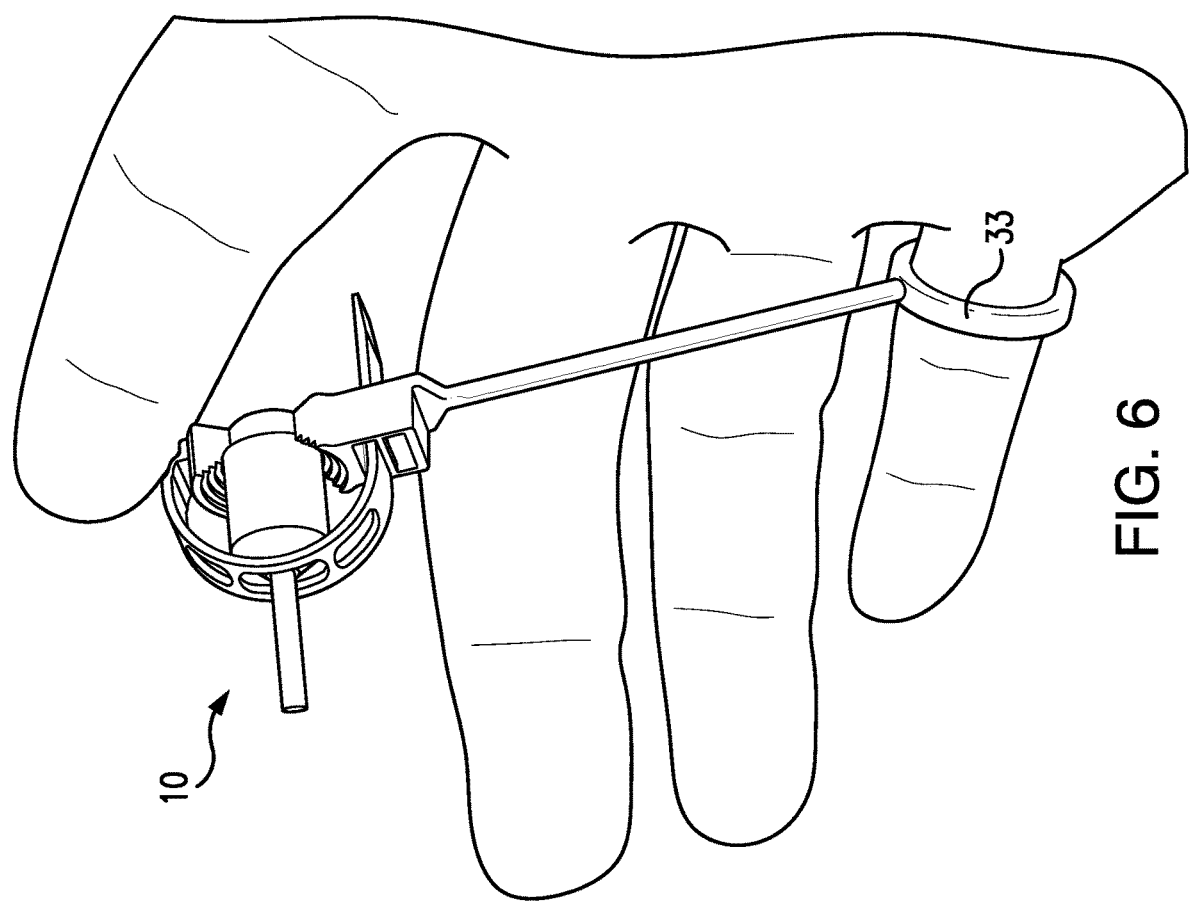

DENTAL IMPLANT SCREWDRIVER HARNESS SYSTEM

FIELD OF INVENTION

The present invention relates to the general field of lanyards and tethers used in connection with hand tools, and more particularly to the field of lanyard/tether systems used to prevent the accidental ingestion or aspiration of small dental tools.

BACKGROUND OF THE INVENTION

With the introduction of implant dentistry and the associated use of small-machined parts and devices, the incidence of a practitioner accidentally dropping a device into a patient's oral cavity has increased. If the patient swallows or aspirates the device, emergency surgical intervention is often necessary, with potentially life-threatening consequences. Screwdrivers used to loosen or tighten abutments to implant fixtures pose a particular hazard, because the dentist must use one hand to both stabilize and turn the driver in the restricted and slippery environment of a patient's mouth. Existing dental isolation measures which block the back of the patient's throat, such as rubber dams and gauze throat screens, have several disadvantages, including patient discomfort and gagging response.

Various lanyard/tether systems have been proposed to mitigate these hazards. Most of these systems involve directly attaching a ligature, such as a string or dental floss, to the screwdrivers head/handle, either by tying it on or inserting it in a bore. But tying is inherently insecure, especially in the slippery environment of an oral cavity, and bores in the driver head require a specially manufactured tool. Moreover, these systems do not offer a good solution to the problem of how to restrain the driver head without interfering with its rotation. As the dentist turns the driver head, the tether wraps around the screwdriver, requiring frequent disentanglement, during which the ligature is apt to shred or detach from the tool.

In response to the entanglement issues with direct attachment ligature systems, some systems interpose a swivel mechanism between the ligature and the driver head. But this measure only further adds to the overall length and bulk of the lanyard, which increases the difficulty of retrieving the tool once it has been dropped into the oral cavity. A long tether/lanyard allows the screwdriver to fall into the throat opening, so that the tool must then be pulled out, thereby injuring the soft tissues of the throat and esophagus.

Therefore, the existing systems are flawed insofar as they merely enable the dentist to retrieve the implant screwdriver once he/she has dropped it—with the retrieval involving potentially traumatic effects. On the other hand, the present invention provides a device which prevents the dentist from losing control of the screwdriver and allowing it to drop into the patient's oral cavity.

SUMMARY OF THE INVENTION

The design of the present invention enables the dentist to restrain and stabilize an implant screwdriver, while simultaneously turning the driver head using only one hand. Instead of tethering to the driver head directly or through a swivel, the tether connects to a stepped socket assembly, comprising multiple driver sockets which seat driver heads of several standard diameters. Attached to one side of the socket assembly is a flexible, slotted driver shaft strap, which wraps over the shaft of the screwdriver and holds the driver head down against its seat in the driver socket.

The combined restraints of the socket and the driver strap secure the screwdriver in place while allowing the driver head to rotate freely, so that the dentist can easily turn it as he/she tightens or loosens an implant abutment. Because the stepped driver sockets comprise opposing circular arcs that are open on both sides, the sockets do not completely encompass the driver head, so that there is ample space for the dentist's fingers to engage the driver head in order to turn it.

Since the driver head is restrained on both ends and cannot become entangled with the tether as it rotates, the tether of the present invention can be shorter than tethers/lanyards that connect directly or through swivels to the driver head. Consequently, even when the dentist's fingers slip off the driver head, the screwdriver cannot fall into the patient's throat, thus obviating the traumatic retrieval process required by the prior art devices.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

BRIEF DESCRIPTION OF THE DRAWINGS

FIG. 1A is a plan view of the obverse side of the first embodiment of the present invention;

FIG. 1B is a side profile view of the first embodiment of the present invention;

FIG. 1C is a plan view of the reverse side of the first embodiment of the present invention;

FIG. 1D is a detail plan view of the driver socket assembly and the strap locking mechanism of the first embodiment of the present invention;

FIG. 6 is a perspective view of one embodiment of the present invention tethered to a user's finger by the finger ring.

DETAILED DESCRIPTION OF THE PREFERRED EMBODIMENT

Figure 2:
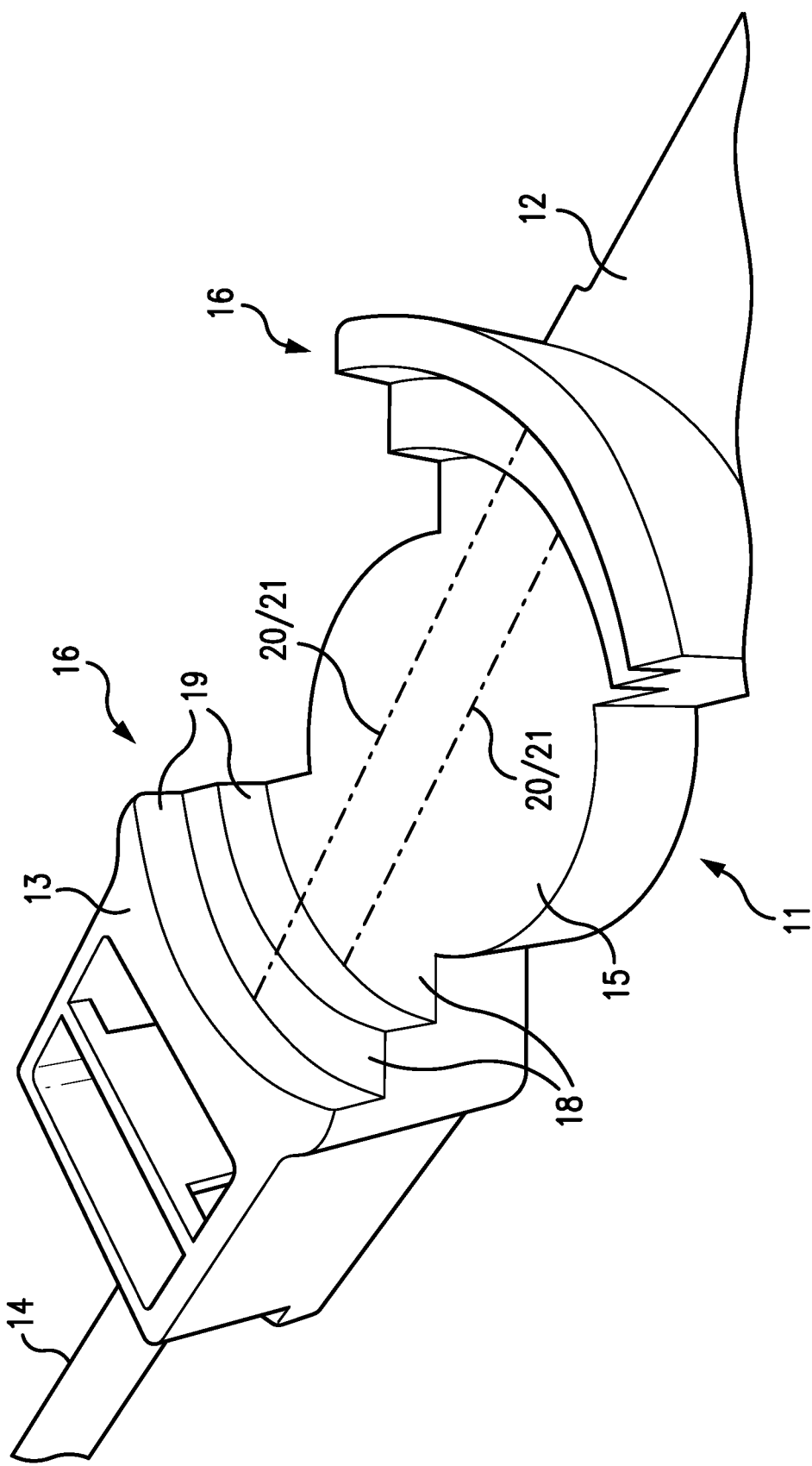
FIG. 2 is a detail perspective view of the driver socket assembly and the strap locking mechanism of the second embodiment of the present invention.

Referring to FIGS. 1A-1D, the first embodiment of the present invention 10 comprises a driver socket assembly 11, a driver shaft strap 12, a strap locking mechanism 13, and a tether member 14.

The driver socket assembly 11 comprises a central socket base 15, which in this embodiment is substantially disk-shaped, and two opposing sets of multiple stepped socket flanges 16 on opposite longitudinal sides of the central socket base 15. The socket flanges 16 are shaped as circular arcs which are concentric with the central socket base 15 and which subtend an acute flange angle 17.

Preferably, the flange angle 17 is greater than 60° and less than 90°. In this embodiment, the flange angle 17 is 80°, so that the driver socket assembly has openings of 100° on either lateral side, through which the dentist can grasp and turn the head of a screwdriver seated in the driver socket assembly 11.

Figure 3A:
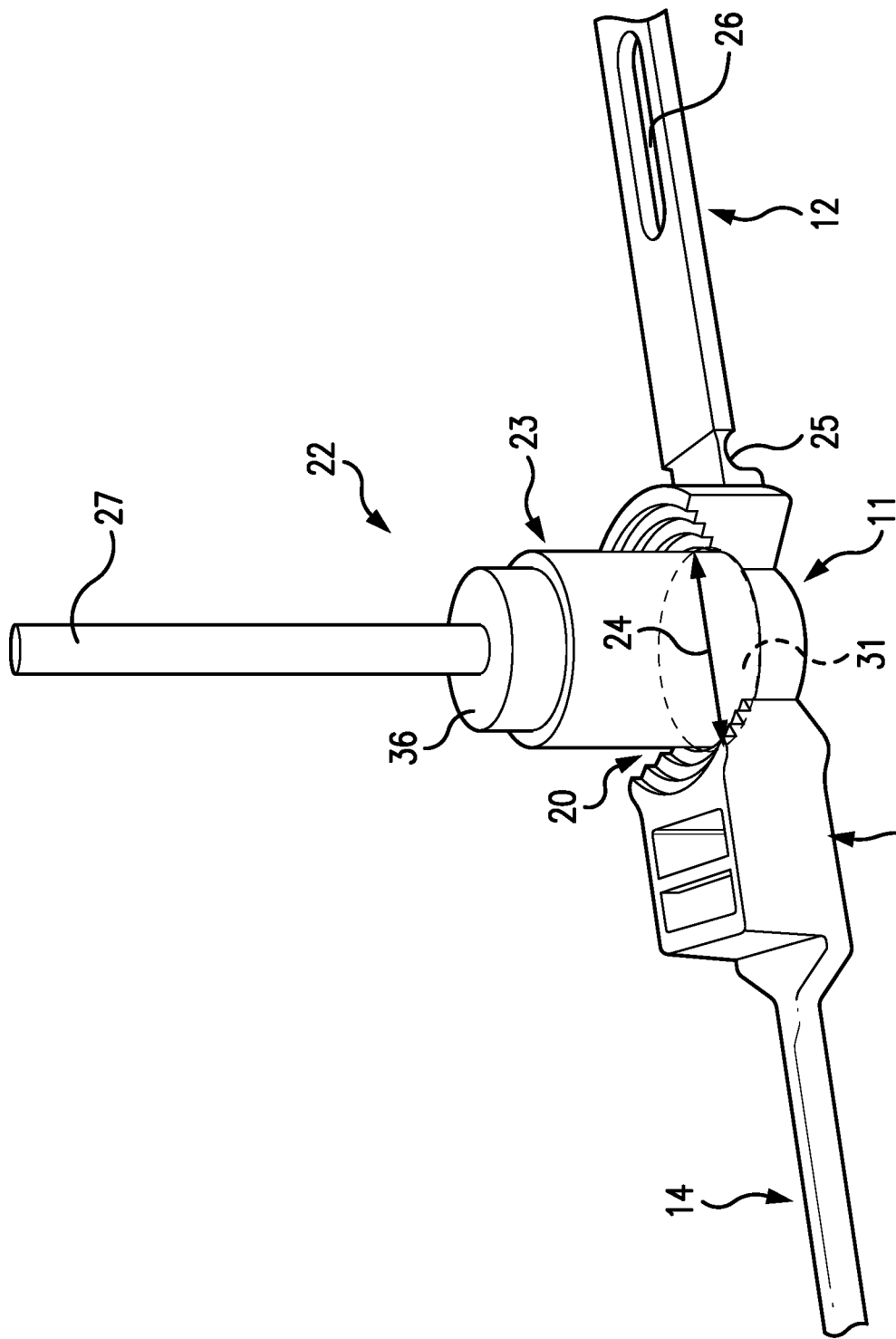
FIG. 3A is a detail perspective view of the driver socket assembly and the strap locking mechanism, with partial views of the driver shaft strap and the tether member, of the first embodiment of the present invention, with a screwdriver seated in the innermost driver socket.
Figure 3B:
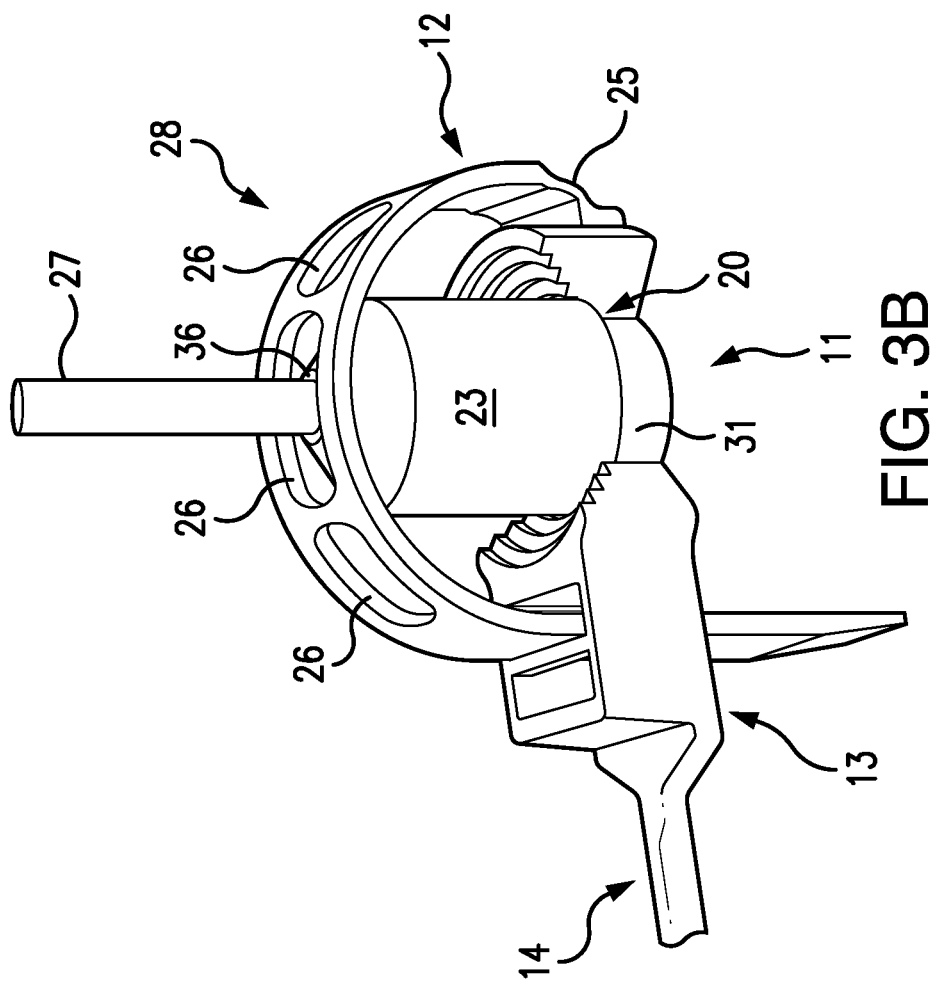
FIG. 3B is a detail perspective view of the driver socket assembly, the strap locking mechanism and the driver shaft strap, with a partial view of the tether member, of the first embodiment of the present invention, with a screwdriver seated in the innermost driver socket, and with the driver shaft strap wrapped over the driver shaft and fixed in the shaft harnessing position by the strap locking mechanism.

The socket flanges 16 form a series of horizontal, circular arcuate flange steps 18, alternating with vertical, circular arcuate flange risers 19, as best seen in FIG. 2. Each of the flange risers 19 cooperates with an opposing flange riser 19 so as to define a driver socket 20, having a socket diameter 21 corresponding to the diameter 24 of the base 31 of the driver head 23 of a screwdriver 22 to be seated in the driver socket 20, as best seen in FIGS. 3A and 3B. Optimally, the flange risers 19 have a height of 0.5 to 1 mm, and the driver socket assembly 11 has a width of 12 to 20 mm.

The driver shaft strap 12 is sufficiently flexible to bend over the top of the driver head 23, as shown in FIG. 3B. The driver shaft strap 12 is hingeably attached to one side of the driver socket assembly 11, and the attachment can comprise a living hinge 25. The driver shaft strap 12 has a longitudinal axis 35 which is aligned with the arc midpoints 34 of the socket flanges 16, and it has multiple oblong strap apertures 26. When the driver shaft strap 12 is wrapped over a screwdriver 22 seated in one of the driver sockets 20, one of the strap apertures 26 slides over and encompasses the driver shaft 27, as depicted in FIG. 3B.

In this shaft harnessing position 28, as shown in FIG. 3B, the driver shaft strap 12 firmly engages the top 36 of the driver head 23 and forces the base 31 of the driver head 23 against the central socket base 15 of the driver socket assembly 11. The seated screwdriver 22 is thereby constrained to axial rotational movements associated with the dentist's manual turning of the driver head 23.

Figure 4:
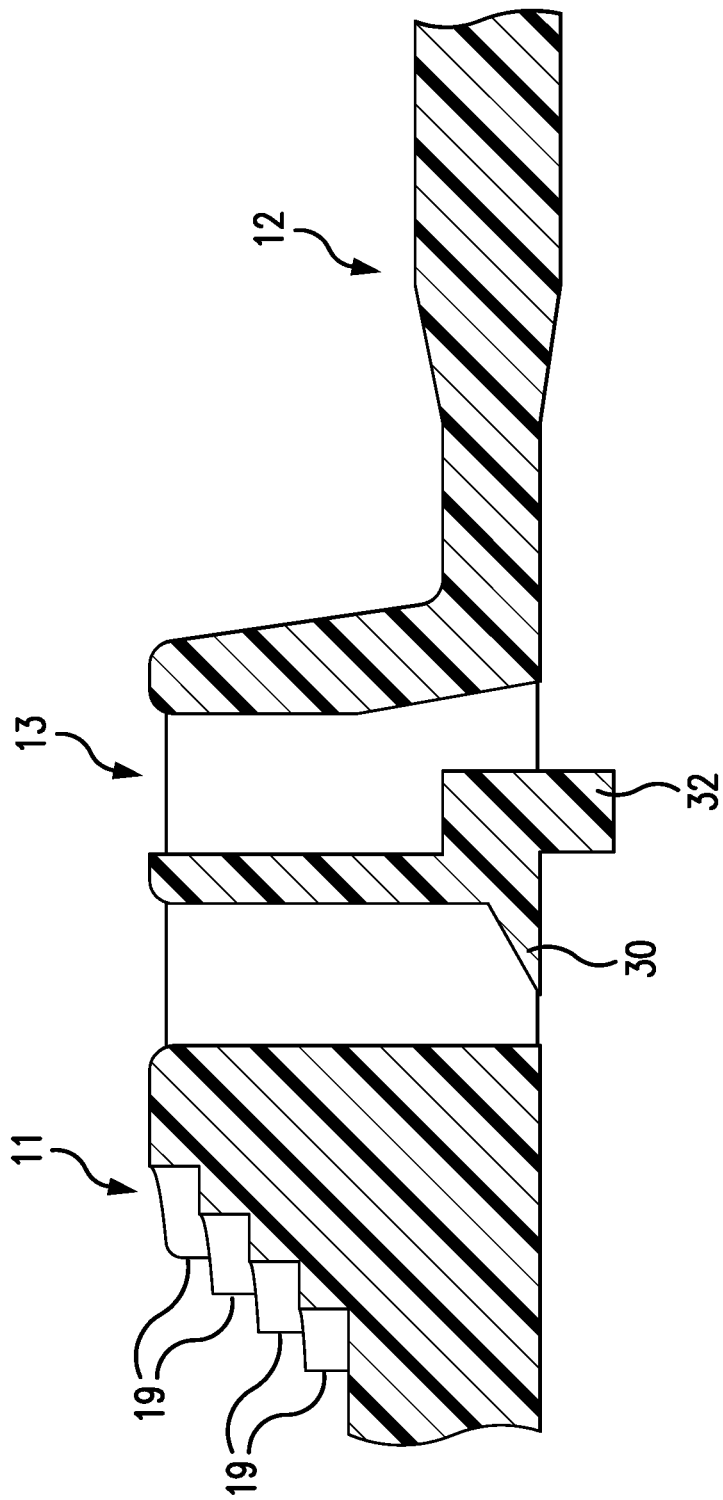
FIG. 4 is a detail perspective view of the strap locking mechanism of the first embodiment of the present invention.

The reverse side of the driver shaft strap 12 contains a series of ridges or projections 29, which conjugately engage the teeth or detents 30 of a strap locking mechanism 13 on the side of the driver socket assembly 11 opposite the driver shaft strap 12. The strap locking mechanism 13 releasably fixes the driver shaft strap 12 in the shaft harnessing position 28. As depicted in FIG. 4, the strap locking mechanism 13 optimally has a release tab 32 which, when manually pushed, releases the teeth/detents of the strap locking mechanism 13 from engagement with the ridges/projections of the driver shaft strap 12, thereby releasing the screwdriver 22 from the harness 10.

Figure 5:
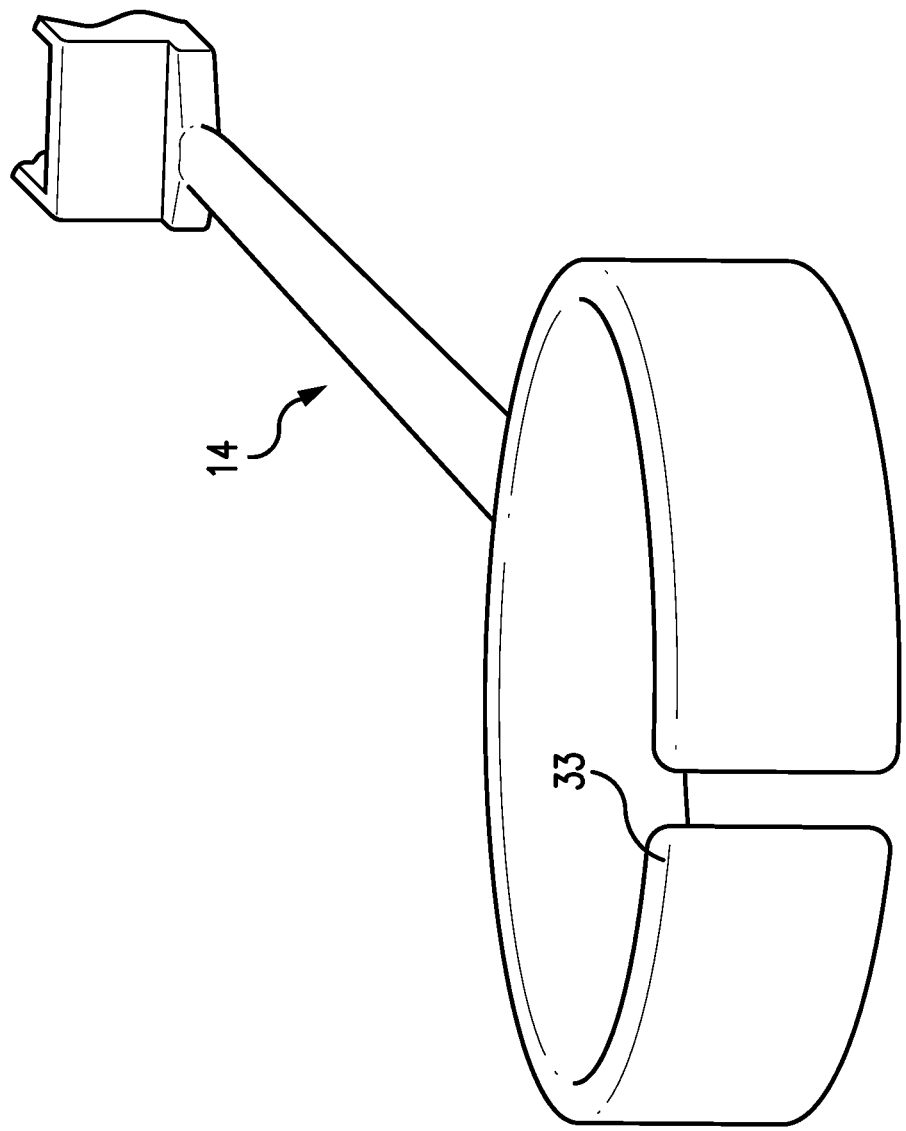
FIG. 5 is a detail perspective view of the split finger ringer of the first embodiment of the present invention.

Extending from the distal side of the strap locking mechanism 13, is the flexible tether member 14, which terminates at its distal end in a split ring 33, best seen in FIG. 5, that attaches to a finger of the dentist's hand, as shown in FIG. 6.

Preferably, the tether member 14 has a length of 70 to 100 mm, and the driver shaft strap 12 has a length of 50 to 60 mm.

The dental screwdriver harness device 10 can be made of a plastic material, and it can optionally be made sterilizable and reusable. Preferably the device 10 would have limited reuse and would be replaced after a number of users.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A device for tethering screwdrivers to a hand of a dental practitioner, the device comprising:
   a driver socket assembly, having two opposite sides, comprising a first side and a second side, and comprising a central socket base, wherein two opposing sets of multiple stepped socket flanges are integrally attached on the opposite sides of the central socket base, and wherein each of the socket flanges forms a circular arc which is concentric with the central socket base and which subtends an acute flange angle, and wherein each of the socket flanges comprises a horizontal, circular arcuate, flange step and a vertical, circular arcuate, flange riser, and wherein each of the flange risers cooperates with an opposing flange riser so as to define a driver socket having a socket diameter corresponding to a diameter of a base of a driver head of a seated screwdriver in the driver socket;
   a flexible driver shaft strap which is hingeably attached to the first side of the driver socket assembly, such that a longitudinal axis of the driver shaft strap aligns with a midpoint of each of the socket flanges, wherein the driver shaft strap has multiple oblong strap apertures, and wherein the driver shaft strap is hinged and configured to enable the driver shaft strap to assume a shaft harnessing position, in which the driver shaft strap is wrapped over the driver socket assembly, such that at least one of the strap apertures slides over and securely encompasses a driver shaft of the seated screwdriver, and such that the driver shaft strap firmly engages a top of the driver head of the seated screwdriver and forces the base of the driver head against the central socket base of the driver socket assembly, thereby constraining the seated screwdriver to an axial rotational movement, and wherein the driver shaft strap contains a series of ridges or projections which conjugately engage one or more teeth or detents of a strap locking mechanism, which is rigidly attached to the second side of the driver socket assembly, so as to releasably fix the driver shaft strap in the shaft harnessing position; and
   a flexible tether member having a proximal end which extends from the strap locking mechanism and having a distal end which is adapted to removably attach to the hand of the dental practitioner.

2. The device according to claim 1, wherein the distal end of the tether member terminates in a ring or a split ring which is adapted to removably attach to a finger of the hand of the dental practitioner.

3. The device according to claim 2, wherein the flange angle is greater than 60° and less than 90°.

4. The device according to claim 3, wherein the tether member has a length of 70 to 100 mm, and the driver shaft strap has a length of 50 to 60 mm.

5. The device according to claim 4, wherein the strap locking mechanism contains a release tab which, when manually pushed, releases the teeth or detents of the strap locking mechanism from engagement with the ridges or projections of the driver shaft strap.

6. The device according to claim 5, wherein each of the flange risers has a height of 0.5 to 1 mm.

7. The device according to claim 6, wherein the width of the driver socket assembly, from the first side to the second side, is 12 to 20 mm.

8. The device according to claim 7, wherein the driver shaft strap is attached to the first side of the drive socket assembly by a living hinge.

9. The device according to claim 8, wherein the device is sterilizable and reusable.

* * * * *